United States Patent
De Coninck et al.

(10) Patent No.: US 9,651,537 B2
(45) Date of Patent: May 16, 2017

(54) METHOD OF MONITORING QUALITY AND/OR AGING OF OIL

(71) Applicant: UNIVERSITÉ DE MONS, Mons (BE)

(72) Inventors: Joel De Coninck, Mons (BE); Sofiene Marouani, Mons (BE)

(73) Assignee: Université de Mons, Mons (BE)

( * ) Notice: Subject to any disclaimer, the term of this patent is extended or adjusted under 35 U.S.C. 154(b) by 180 days.

(21) Appl. No.: 14/414,483

(22) PCT Filed: Jul. 11, 2013

(86) PCT No.: PCT/EP2013/064679
§ 371 (c)(1),
(2) Date: Jan. 13, 2015

(87) PCT Pub. No.: WO2014/009471
PCT Pub. Date: Jan. 16, 2014

(65) Prior Publication Data
US 2015/0192558 A1 Jul. 9, 2015

(30) Foreign Application Priority Data
Jul. 13, 2012 (GB) .................................. 1212542.3

(51) Int. Cl.
G01N 33/28 (2006.01)
G01N 29/02 (2006.01)

(52) U.S. Cl.
CPC ............. G01N 33/28 (2013.01); G01N 29/02 (2013.01); G01N 29/022 (2013.01);
(Continued)

(58) Field of Classification Search
CPC ... G01N 2291/0226; G01N 2291/0258; G01N 2291/02818; G01N 29/02; G01N 29/022; G01N 33/28; G01N 33/2888
See application file for complete search history.

(56) References Cited

U.S. PATENT DOCUMENTS 6,151,956 A * 11/2000 Takahashi ............ G01N 29/024
73/10
6,223,589 B1 * 5/2001 Dickert .................. G01N 11/16
310/311

(Continued)

OTHER PUBLICATIONS

Lieberzeit et al: "Nanoparticles for detecting pollutants and degradation processes with mass-sensitive sensors", Sensors and Actuators B: Chemical: International Journal Devoted to Research and Development of Physical and Chemical Transducers, Elsevier S.A., Switzerland, vol. 127, No. 1, Oct. 5, 2007 (Oct. 5, 2007), pp. 132-136,XP022286090, ISSN: 0925-4005, DOI: 10.1016/J.SNB.2007.07.020 p. 133, left-hand column, paragraph 4.

(Continued)

*Primary Examiner* — Francis Gray
(74) *Attorney, Agent, or Firm* — Jerold I. Schneider; Schneider Rothman Intellectual Property Law Group, PLLC

(57) ABSTRACT

The quality and/or aging of an oil is monitored, notably in-situ, using a resonator sensor, for example a quartz crystal microbalance sensor (QCM). Changes of the frequency response of the sensor may be used to detect or monitor the presence of one or a combination of water, fuel, metallic debris, plastic debris and reaction products from degradation of oil components and/or oil additives (including oxidation products and acids). At least one of the major surfaces of the resonator sensor may include a component capturing surface layer provided with impression sites adapted to retain components of the oil indicative of the oil's quality, aging or contamination and both major surfaces of the sensor are preferably immersed in the oil to be monitored.

19 Claims, 2 Drawing Sheets

Figure 1:
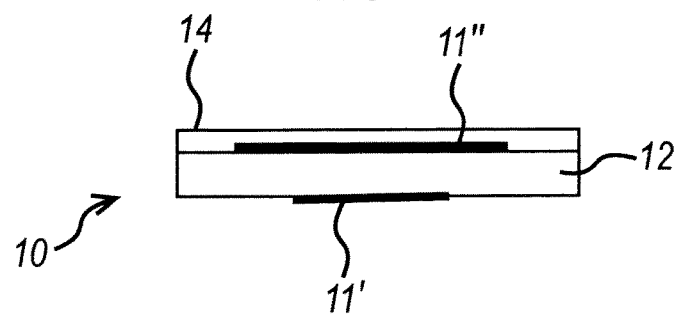

(52) U.S. Cl.
CPC . *G01N 33/2888* (2013.01); *G01N 2291/0226* (2013.01); *G01N 2291/0258* (2013.01); *G01N 2291/02818* (2013.01)

(56) References Cited

U.S. PATENT DOCUMENTS

| | | | | |
|---|---|---|---|---|
| 7,541,004 | B2* | 6/2009 | Niksa | G01N 27/126 324/698 |
| 2003/0062910 | A1* | 4/2003 | Wang | G01N 27/06 324/698 |
| 2009/0115416 | A1* | 5/2009 | White | G01N 24/08 324/316 |
| 2015/0075268 | A1* | 3/2015 | Qi | G01N 27/22 73/114.55 |

OTHER PUBLICATIONS

Peter A. Lieberzeit et al: "Bioanalogous Recognition with Sol-Gel Thin Films and Nanoparticles in Harsch Environments", MRS Proceedings, vol. 1094, Jan. 1, 2008 (Jan. 1, 2008), XP055075029, DOI: 10.1557/PROC-1094-DD05-08 the whole document.

Peter A Lieberzeit et al: "Molecularly imprinted sol-gel nanoparticles for mass-sensitive engine oil degradation sensing", Analytical and Bioanalytical Chemistry, Springer, Berlin, DE, vol. 389, No. 2, May 3, 2007 (May 3, 2007), pp. 441-446, XP019537475, ISSN: 1618-2650, DOI: 10.1007/S00216-007-1274-3 p. 442, left-hand column, paragraph 2, right-hand column paragraph 2.

Mujahid A et al: "Imprinted sol-gel materials for monitoring degradation products in automotive oils by shear transverse wave", Analytica Chimica Acta, Elsevier, Amsterdam, NL vol. 675, No. 1, Aug. 18, 2010 (Aug. 18, 2010), pp. 53-57, XP027206725, ISSN: 0003-2670 [retrieved on Jul. 15, 2010]p. 54, left-hand column, paragraph 3-right-hand column, paragraph 2.

P.A. Lieberzeit et al: "Nanostructured polymer for detecting chemical changes during engine oil degradation", IEEE Sensors Journal, vol. 6, No. 3, Jun. 1, 2006 (Jun. 1, 2006), pp. 529-535, XP055075034, ISSN: 1530-437X, DOI: 10.1109/JSEN.2006. 872341, p. 529, right-hand column, paragraph 4-p. 530, right-hand column, paragraph 1.

* cited by examiner

METHOD OF MONITORING QUALITY AND/OR AGING OF OIL

CROSS-REFERENCE TO RELATED APPLICATIONS

This application is the entry into the United States of PCT Application No. PCT/EP2013/064679 filed Jul. 11, 2013 and claims priority from Great Britain Patent Application No. GB1212542.3 filed Jul. 13, 2012, the entirety of each of which are hereby incorporated by reference.

This invention relates to in situ monitoring of the quality and/or aging state of lubricating and/or cooling oil particularly in high load machinery and to associated sensors. It is particularly appropriate for assessing the aging state and/or contamination of oil in aeronautic engines, aeronautic hydraulic systems and industrial power generating turbines.

In view of the complex mixtures of oil and additives often used in high load machinery and the various possible sources of in-use contamination, measurement of a single parameter has proved an unreliable indicator for monitoring oil quality and degradation. For example, although systems have been proposed for monitoring oil viscosity as an indication of aging, the degradation of some oil components may increase viscosity, whilst degradation of other oil components may reduce viscosity and fuel or water contamination may also have significant effects on the viscosity. Chemical analysis by titration of a used oil, for example to determine the Total Base Number or Total Acid Number, may provide a more reliable indication of the aging state of the oil but is not suited to in-situ or real time measurements.

The idea of capturing specific components of an automotive oil on the surface of a quartz micro balance sensor (QCM) and using the frequency shift of the QCM as an indication of a varying concentration of those components in the oil has been known for some time. For example, U.S. Pat. No. 6,223,589 discloses a QCM sensor intended for on board determination of aging in the oil of an automotive combustion engine. A chemically sensitive surface layer produced by molecular imprinting of different polyurethanes is provided on a surface of the QCM sensor; at least one specific analyte which is a motor oil constituent is releasably absorbed or adsorbed at this surface layer and a shift in frequency of the quartz micro balance indicative of the amount of specific analyte present is used to monitor oil aging. The disclosure of WO 2004/043773 is similar but proposes a sensitive surface layer of a ceramic silicate polymer. In these types of QCM sensor systems, the face of the QCM sensor at which the sensitive surface layer is provided is immersed in the oil to be monitored and the opposite face is generally isolated and remains in contact with air. Despite the possibilities offered by these proposed QCM sensors, they have not been widely used.

According to one of its aspects, the present invention provides a method of monitoring the quality and/or aging of an oil in situ as defined in claim 1. Other aspects are defined in other independent claims. The dependent claims define preferred or alternative embodiments.

The present invention may be used to monitor oil quality, for example to allow for oil replacement at an appropriate time; it may be used to detect or monitor the presence of one or a combination of water, fuel, metallic debris, plastic debris and reaction products from degradation of oil components and/or oil additives (including oxidation products and acids). The monitoring may be in-situ and/or continuous.

According to one of its aspects, the present invention may use a sensor which is adapted to resonate when subjected to an electrical excitation signal, particularly a quartz crystal microbalance sensor. At least one face of the sensor comprises a component capturing surface layer adapted to capture and retain components of the oil indicative of the oil's quality, aging or contamination. The capture and retention of these components (for example by incorporation or inclusion) affects the resonant frequency of the resonator sensor and a frequency shift of the sensor may be used as an indication of the quantity or mass of components captured and retained and thus as an indication of the amount or concentration of these components in the oil being monitored.

Preferably, the components are releasably retained. Preferably, the quantity or concentration of the components captured and retained is a function of the quantity or concentration of the said components in the oil being monitored, preferably with an equilibrium maintained between the quantity or concentration of the components captured and retained and the quantity or concentration of the said components in the oil being monitored. In this way, a sensor which has captured and retained components from used oil will release these components when contacted with fresh, unused oil.

The impression sites may be provided by cavities adapted to receive and retain particular components.

The impression sites may be provided on particles which are secured to the sensor; this facilitates provision of a high density of impression sites per surface area of sensor; it also facilitates accessibility of the impression sites for components to be captured and retained. The use of inorganic particles enables the component capturing surface layer to withstand in-situ operating conditions in high load machinery. For example, the temperature of the liquid, particularly oil, with which the sensor is in contact may be $\geq 50°$ C., $\geq 60°$ C., $\geq 70°$ C., $\geq 80°$ C., $\geq 100°$ C., $\geq 150°$ C. or $\geq 200°$ C. The sensor is preferably adapted to withstand (but not necessarily operate at) temperatures within the range of $-20°$ C. to $180°$ C.

The component capturing inorganic particles preferably comprise or consist essentially of titanium dioxide as this has proved particularly adapted to the combined requirements of the provision of impression sites, facility of being secured to the sensor and withstanding desired operating conditions for in-situ oil monitoring. Alternatively or additionally, other inorganic particles may be used, for example particles which comprise or consist essentially of silicon dioxide.

At least 90% and preferably at least 95% of the inorganic particles preferably have a diameter of less than 250 nm, more preferably less than 200 nm; at least 90% and preferably at least 95% of the inorganic particles preferably have a diameter of at least 25 nm, preferably at least 50 nm, more preferably at least 75 nm; this improves the sensitivity of the sensor. The particles used may be selected according to their diameter from a larger set of particles, for example by filtration to retain only particles having a diameter within a desired range.

Whilst increasing the quantity of inorganic particles would increase the sensitivity of the sensor, care should be taken to avoid overloading the sensor in a way in which excessive added mass would prevent it from functioning correctly and/or predictably. For this reason, the quantity of particles used on the sensor with respect to the area of the sensor provided with the component capturing surface layer is preferably $\leq 4$ mg/cm$^2$, more preferably $\leq 2$ mg/cm$^2$; it is preferably ≥0.2 mg/cm², more preferably ≥0.4 mg/cm². More preferably, the quantity of particles used is about 0.6 mg/cm² (±0.4 mg/cm²), for example, a quantity of 3 mg (±2 mg) has been found particularly suitable for a disc shaped sensor having a diameter of about 25 mm with the component capturing surface layer provided over the entire major surface on a single side of the sensor.

A securing material may be used to secure the component capturing inorganic particles to the sensor and may be provided as a layer, preferably a layer from which the particles project. It may be an inorganic material and may comprise or consist essentially of titanium dioxide or silicon dioxide. The use of an inorganic material helps ensure stability at high temperatures.

Components that may be used as an indicator of the oil's aging may be selected from the group consisting of capric acid, fatty acids, fatty alcohols, fatty aldehydes and ketones, fatty peroxides and fatty esters, and combinations thereof; these components may be used for molecular imprinting. One or more oxidation products indicative of used oil may be used. The component indicative of the oil's quality, aging or contamination preferably comprise a mixture of components, notably a combination of the aforementioned components, which together provide a more representative indication. Preferably, the impression sites are produced on the basis of a sample representative of a used oil. For example, the components which together provide a representative indication may be one, two, three, four or more components selected from components expected to be present in the used oil. The indicator component(s) may be selected as a function of a particular type, quality or composition of oil which is to be monitored and/or may be selected based on chemical analysis of an oil to be monitored, notably a used oil, for example by high-performance liquid chromatography (HPLC). Alternatively, or additionally, the impression sites may be produced by using a used oil for molecular imprinting. Such a used oil may be an aeronautical oil that has been used in service in an aeronautical engine (for example for at least 150, 200, 250, 300 or 350 hours) or an oil that has been aged in laboratory conditions. The impression sites may be arranged to be responsive to an increase in the concentration of carbonyl groups and/or a decrease in the concentration of antioxidants, each of which may give an indication of oil aging.

In some embodiments, the use of two or more types of component capturing particles allows a single sensor to be responsive to distinct forms of aging and/or contamination. For example, one type of component capturing particle receptive to a mixture of components of used oil may be used with another type of component capturing particle receptive to fuel or water present in oil so that the single sensor is independently responsive to oil aging components and fuel or water contamination. Alternatively, or additionally, two separate sensors may be used together, one sensor being receptive to one component or set of components (for example at least one component indicative of used oil) and the other sensor being receptive to another component or set of components (for example different component(s) indicative of used oil or a component indicative of fuel or water contamination in oil).

It has been found that using titanium dioxide allows extremely complex cavities characteristic of a used oil to be produced.

The presence of impression sites, particularly when they are provided by cavities formed for example by molecular imprinting, may be deduced by a difference in resonant frequency of the sensor under similar conditions in fresh oil and in used oil and/or by observing a change in the concentration of one or more oil components indicative of oil aging when an oil sample of know composition in respect of said components is passed over the sensor.

An atomic force microscope may be used to observe the morphology of the component capturing surface layer.

The ability to use a sensor in-situ such that both major surfaces and/or the entire sensor is immersed in the oil to be monitored provides a simplified and practical arrangement particularly in situations in which the pressure of the oil to be measured is greater than atmospheric pressure, for example at a pressure≥3 bars, ≥4 bars, ≥5 bars, ≥6 bars, ≥8 bars or ≥10 bars. This may be used to avoid differences in hydrostatic pressure across the resonator sensor which would affect the operation of the sensor and/or cause its breakage. The sensor may be used at a pressure in the range 6 to 15 bars.

In order to facilitate mounting of the sensor such that both major surfaces and/or the entire sensor is immersed in the oil to be monitored, each electrode of the sensor may be connected, for example by soldering, to one end of an electrical wire, the other end of which is adapted for connection to a remotely positioned controller, for example via a BCN connector. Insulation of these connections and/or of the electrodes may be provided to avoid the risk of short circuits or electrical leakages when the sensor is immersed in a liquid whose electrical conductivity may cause such risks. Nevertheless, such insulation has been found generally unnecessary in respect of monitoring of fresh and used oils, particularly where the resistance of the oil is greater than 100 MΩ (which was the detection limit of a multimeter used to measure the resistance of fresh and used oils in tests).

Rendering the securing material substantially impermeable to oil reduces the risk of oil being adsorbed or absorbed at the securing material which would have an influence on the mass and thus frequency response of the sensor. Such unselective capturing of oil components would decrease the overall sensitivity of the sensor with respect to the components of the oil indicative of the oil's quality, aging or contamination. In particular, the securing material is preferably substantially free from cracks and/or micro-cracks which could retain oil components; conditions for deposition and/or treating the securing material should be selected to achieve this. In the case of a spun coating it is desirable to optimise and control the nature and concentration of the precursor solution and the speed of the spin coating. The spin coating may be carried out at an angular velocity≥1500 rpm, ≥2000 rpm, or ≥2500 rpm and/or ≤5000 rpm, ≤4500 rpm or ≤3500 rpm. The average thickness of the component capturing surface layer may be ≥0.5 μm or ≥0.8 μm and/or ≤2 μm or ≤1.5 μm.

Particularly in the case of sol gel coatings it is desirable to optimise and control the drying conditions (including temperature, and duration) so as to avoid cracking. Preferably, pre-treatment at a temperature≥50° C. or ≥80° C. and/or ≤150° C. or ≤120° C. for a duration≥5 minutes or ≥8 minutes and/or ≤30 minutes, or ≤20 minutes is used to reduce the risk of cracking of the coating during a subsequent heat treatment intended to cross-link and/or stabilise the coating. The pre-treatment may be carried out in a liquid, for example in boiling water. The heat treatment intended to cross-link and/or stabilise the coating may comprise subjecting the coating to:

a temperature≥120° C. or ≥140° C. and/or ≤200° C. or ≤180° C. for a duration≥10 hours or ≥15 hours and/or ≤ to 30 hours, or ≤25 hours;

and optionally subsequently subjecting the coating to:
a temperature≥250° C. or ≥300° C. and/or ≤450° C. or ≤400° C. for a duration≥5 minutes and/or ≤ to 30 minutes or ≤20 minutes.

A hydrothermal treatment comprising immersing the coating in boiling water for 10 minutes, followed by subjecting the sensor to a temperature of 160° C. for about 20 hours and then to a temperature of about 350° C. for 10 minutes has given good results.

A monitor sensor may be used by itself to monitor oil; in this case, the sensor's frequency response may be compared against a reference and/or historical frequency response and/or its frequency response at a known temperature may be compared to a reference response at the same temperature. Preferably however, a monitor sensor is used in association with a reference sensor which is exposed to substantially the same conditions, for example by mounting the two sensors adjacent to each other in the oil to be monitored, the reference sensor being substantially similar to the monitor sensor but not having impression sites adapted to retain components of the oil. Such an arrangement allows a differentiation to be made between the frequency shift of the monitor sensor resulting from capture and retention of oil components and the frequency shift due to other factors (notably viscosity and/or temperature) to which the reference sensor will also be subjected. The reference sensor may be provided with a surface layer similar to that of the monitor sensor (but without or substantially without impression sites) so as to minimise other differences between the two sensors. It may be useful, especially in the case of a single sensor being used by itself, to provide a temperature compensation so as to allow the effect of the measurement temperature to taken in to account when interpreting the sensor's output.

In some embodiments of the invention, transient variations in the vibration of a sensor, preferably a sensor as described above, indicative of the presence of debris in the oil, for example, metallic and/or plastic debris are monitored and used to provide an indication of contamination. Debris monitored may have a diameter≥20 µm or ≥50 µm or ≥100 µm and/or ≤1000 µm or ≤800 µm or ≤600 µm. Generally, a signal derived from monitoring the vibration of the sensor will include background noise; a shift in frequency indicative of the passage of debris in the vicinity of the sensor may be at least three times the amplitude of the background noise. Such a frequency shift may have a duration of ≥5 seconds or ≥3 seconds or ≥1 seconds and/or ≤0.01 seconds or ≤0.05 seconds prior to the frequency of the vibration of the sensor returning substantially to its previous steady state value.

In a further embodiment, the presence and nature of debris, particularly a liquid debris may be deduced. For example, the presence of fuel (e.g. kerosene) in oil may produce a transient variation in the vibration of a sensor as the portion of fuel approaches a sensor, and when the sensor (or another sensor) is provided with a material which attracts and/or incorporates fuel, a change in the steady state vibration of that sensor may be used to provide an indication of the presence of fuel. Such an arrangement may alternatively or in addition be used in relation to other liquid debris, for example, water.

The sensor may be adapted to have a resonant frequency in air at normal atmospheric conditions of about 5 MHz±1 MHz.

Figure 2:
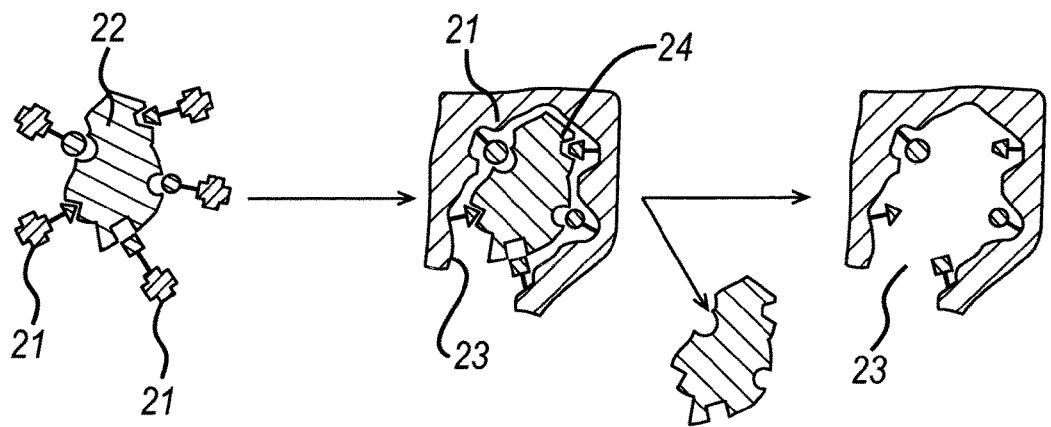
Figure 3:
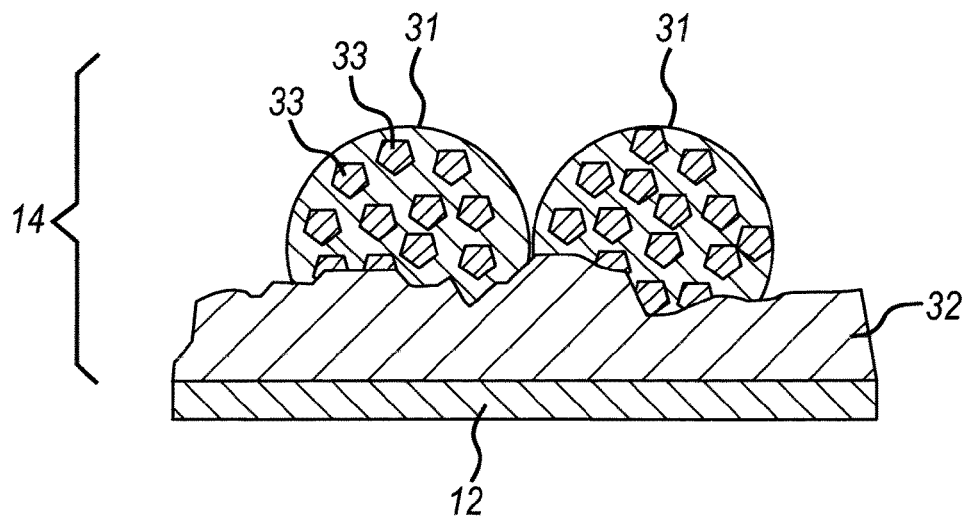
Figure 4:
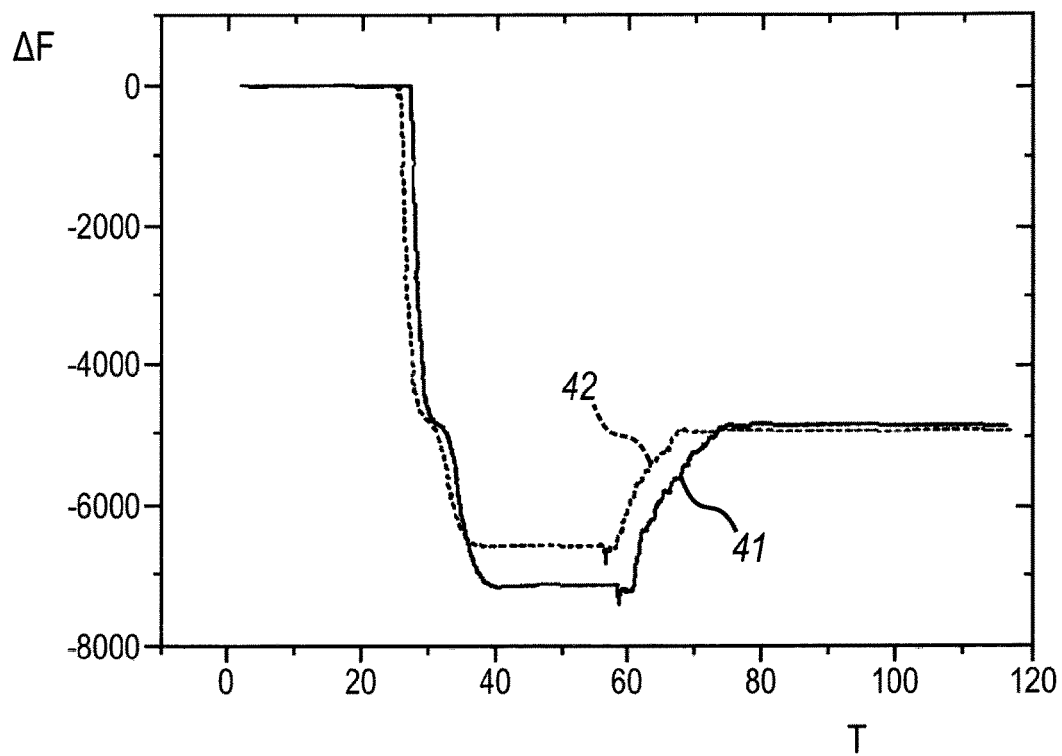
Figure 5:
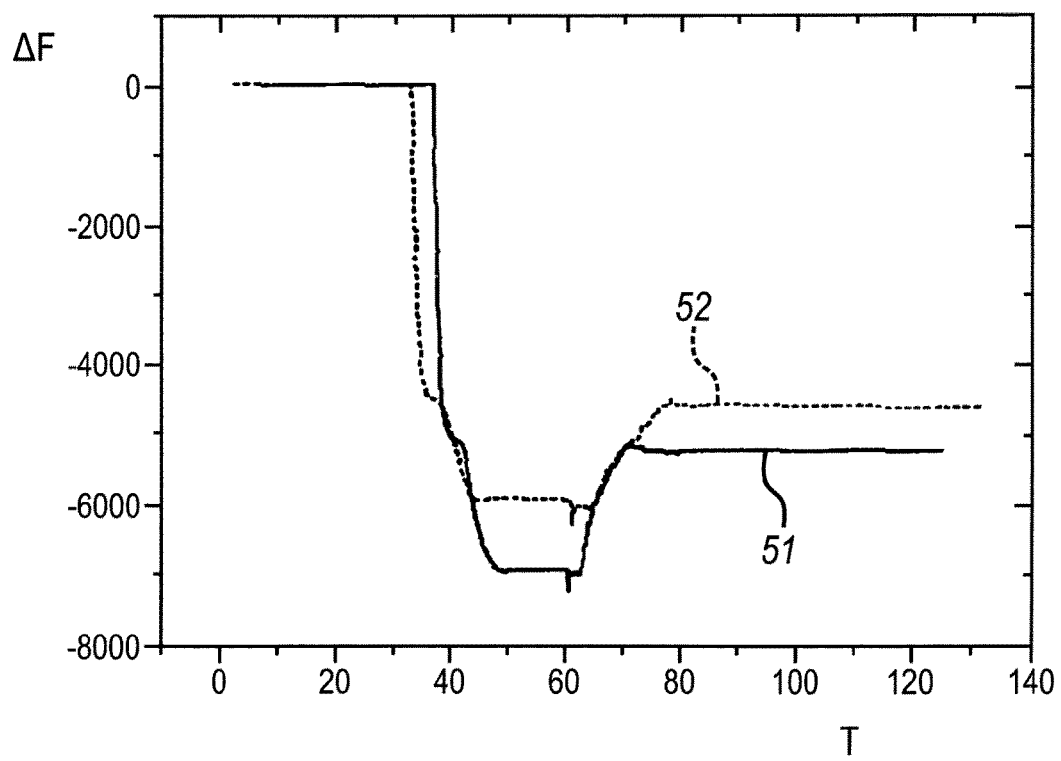

An embodiment of the invention will now be described, by way of example only, with reference to the accompanying drawings, of which:

FIG. 1 is a schematic cross section view of a sensor;
FIG. 2 is a schematic representation of the principle of molecular impression;
FIG. 3 is a schematic cross section of a portion of the sensor surface; and
FIG. 4 and FIG. 5 are graphs showing frequency responses of sensors.

The sensor 10 of FIG. 1 is a disc shaped AT-cut quartz crystal microbalance sensor (QCM) (diameter about 25 mm, thickness about 330 µm) each major surface of which is provided with a gold electrode 11', 11" of different diameter such that application of an appropriate AC voltage across the electrodes causes vibration of the quartz disc 12 (a standing shear wave) at a resonant frequency. An electrical connection (not shown) provides an electrical connection between each electrode 11', 11" and a crystal controller, for example via a BCN or other suitable connector, with the crystal controller being configured to supply an AC voltage across the electrodes and to measure the vibration frequency of the sensor using an oscillator circuit. The resonant frequency is influenced by a plurality of factors including the thickness of the layer of quartz of the sensor, its cross sectional form, its mass, the temperature and physical properties of the fluid(s) with which it is in contact.

One surface of the sensor, notably the surface provided with the larger diameter electrode, is provided with a component capturing surface layer 14 comprising, in this embodiment inorganic titanium dioxide nano-particles 31 secured to the sensor by a titanium dioxide securing material 32 (see FIG. 3). The inorganic nano-particles 31 are provided with impression sites 33 comprising cavities produced by molecular imprinting.

FIG. 2 illustrates the principle of molecular imprinting. In this embodiment, titanium dioxide 21 is synthesised from a solution of titanium tetrachloride ($TiCl_4$) in the presence of one or more types of oil component 22. Addition of water with vigorous agitation results in the formation of titanium dioxide. As a portion of the titanium dioxide 21 forms around an oil component 22, it creates a cavity having a form which mirrors the form and/or fixation points 24 of the oil component. The portion of titanium dioxide comprising this cavity it then agglomerated with other portions to form a particle 31 of $TiO_2$ (as shown in FIG. 3) which has multiple impression sites 33. The particles may be separated and collected by centrifugation. Once the particles 31 have been formed, the oil components 22 around which the impression sites have been formed are removed. For example in the case of capric acid being used as the oil components 22 around which the impression sites have been formed, the capric acid may be removed by washing with toluene or by evaporation, for example by heating in an oven at about 400° C. Each impression site provides a "memory cavity" having the ability to selectively capture and at least temporarily retain (ie incorporate) molecules of a form or type identical to and/or similar to the oil component 22 around which it was formed when in contact with oil containing such molecules.

Whilst it is possible to provide impression sites directly in a coating layer applied to the sensor, for example in a titanium dioxide layer deposited by spin coating, the use of particles 31 provided with impression sites 33 provides a greater number of impression sites per surface area of the sensor than a simple layer; this may be used to provide greater sensitivity to the sensor. Furthermore, decoupling the operations of (a) creating a material with appropriate impression sites and (b) securing the material having appropriate impression sites to the sensor provides greater manufacturing flexibility.

The particles 31 are secured to a surface of the sensor by a securing material, for example a layer of titanium dioxide 32 deposited, for example by a sol-gel technique, preferably by spin coating. In one embodiment a precursor for the securing material is prepared by dissolving an alkoxyde, particularly titanium tetraisopropoxide $Ti_4(OCH_3)_{16}$ and/or titanium butoxide $Ti(OBu)_4$ in an alcohol (eg ethanol or propanol) in the presence of a catalyst (eg $TiCl_4$), for example at ambient temperature over 20 hours. Pre-formed $TiO_2$ particles provided with impression sites are put in a suspension solution, for example ethanol and/or propanol, to which the prepared precursor for the securing material is added. This mixture is then used to coat a surface of the sensor by spin coating with a subsequent heat treatment of the spun coating being used to improve the adhesion of the coating and thus of the $TiO_2$ particles to the sensor. A "Laurell" device model WS-650 MHz-23NPP/LITE was used at an angular velocity of 3000 rpm and an acceleration of 224 rpm per second to obtain a spun-coating having a thickness of about 1 μm. A heat treatment of immersion of the coated sensor in boiling water, notably for about ten minutes, has been found to reduce the risk of forming cracks during subsequent heat treatment, for example a thermal treatment intended to cross-link and/or stabilise the component capturing surface layer. A suspension containing about 5 mg (±2 mg) of particles for coating a face of a 25 mm diameter QCM has given good results.

As illustrated in FIG. 3, the coating 14 on the sensor is arranged so that a significant portion and preferably a majority of the surface of the particles 31 projects above the layer of securing material 32 so as to expose a large number of impression sites 31. Impression sites may be provided in the securing material, for example during deposition of a layer of the securing material.

FIG. 4 and FIG. 5 show the difference in vibration frequency (ΔF) in Hz (with respect to resonant frequency in air) against time (T) in seconds of a quartz microbalance sensor having each of its two major surfaces immersed in fresh aeronautic engine oil (lines 41 and 51) and used aeronautic engine oil (lines 42 and 52) when excited using a QCM25 crystal oscillator associated with a QCM200 Quartz Crystal Microbalance Digital Controller (both manufactured by Stanford Research Systems). In each case, a stable resonant frequency is established after about 80 seconds. In FIG. 4, an ordinary QCM sensor (not having a component capturing surface layer) is used and little difference between the resonant frequencies in fresh 41 and used 42 oil is observed. In FIG. 5, a QCM sensor having a component capturing surface layer is used and a frequency shift of about 660 Hz is observed with respect to the resonant frequencies in fresh 51 and used 52 oil. This frequency shift is due to components in the used oil (which are not present in the fresh oil or are present only to a lesser degree) being captured and retained at the impression sites 33 of the $TiO_2$ particles thus increasing the mass of the component capturing surface layer of the sensor and lowering the resonant frequency of the sensor.

The invention claimed is:

1. A method of monitoring the presence of contaminant in a liquid comprising:
   exciting a resonator immersed in the liquid so as to establish a steady state vibration response;
   monitoring the steady state vibration response of the sensor so as to detect a transient disturbance in the steady state vibration response indicative of the passage of a contaminant in the proximity of the resonator.

2. The method of claim 1, in which the liquid is oil and in which the contaminant is at least one contaminant selected from the group consisting of solid debris, metallic debris, plastic debris, fuel, kerosene and water.

3. The method of claim 1, in which the resonator sensor has two major surfaces and both major surfaces of the sensor are immersed in the liquid.

4. The method of claim 1, in which
   the resonator sensor comprises a component capturing surface layer provided with impression sites adapted to retain components of the liquid indicative of the liquid's quality, aging or contamination and
   in which the method comprises the additional step of monitoring the resonant frequency of the resonator sensor so as to detect a long term change in the resonant frequency.

5. The method of claim 1, in which the duration of the transient disturbance is 3 seconds.

6. The method of claim 1, in which the amplitude of the transient disturbance used to indicate the presence of a contaminant is at least three times the amplitude of an average of the background noise of the signal.

7. The method of claim 1, in which the method uses a sensor for in-situ monitoring of the quality and/or the aging of oil,
   the sensor being adapted to resonate when subjected to an electrical excitation signal, the sensor comprising
      a component capturing surface layer comprising component capturing inorganic particles provided with impression sites adapted to incorporate components of the oil indicative of the oil's quality, aging or contamination,
      the component capturing particles being secured to the sensor by a securing material.

8. The method of claim 7, in which the impression sites of the said sensor are produced by molecular imprinting.

9. The method of claim 7, in which the impression sites of said sensor are adapted to retain a set of components of the oil,
   the said set of components of the oil comprising a plurality of different oil components which together provide an indication which is indicative of the oil's quality, aging or contamination.

10. The method of claim 7, in which the impression sites of said sensor are produced by molecular imprinting from at least one and preferably a plurality of components selected from the group consisting of capric acid, used oil components, and used oil.

11. The method of claim 7, in which the impression sites of said sensor are produced by molecular imprinting from at least one and preferably a plurality of components selected from the group consisting of fatty acids, fatty alcohols, fatty aldehydes and ketones, fatty peroxides and fatty esters.

12. The method of claim 7, in which the said sensor has at least one of the following features:
   (a) the component capturing inorganic particles comprise particles of titanium dioxide;
   (b) the securing material comprises a layer of an inorganic material;
   (c) the securing material comprises a layer of titanium dioxide;
   (d) the component capturing surface layer is produced by applying a mixture comprising the component capturing inorganic particles and precursors of the securing material to a surface of the sensor;
   (e) the securing material is substantially impermeable to the oil;

(f) the component capturing surface layer comprises two or more types of component capturing inorganic particles, each type of component capturing inorganic particle being adapted to retain a different component or different combination of components of the oil indicative of its quality, aging or contamination.

13. A method of monitoring the quality and/or aging of an oil in-situ, comprising:

providing a resonator sensor having two major surfaces,
at least one of the major surface of the resonator sensor comprising
a component capturing surface layer provided with impression sites adapted to retain components of the oil indicative of the oil's quality, aging or contamination; and immersing both major surfaces of the sensor in the oil to be monitored in which the method uses a sensor for in-situ monitoring of the quality and/or the aging of oil, the sensor being adapted to resonate when subjected to an electrical excitation signal, the sensor comprising
a component capturing surface layer comprising component capturing inorganic particles provided with impression sites adapted to incorporate components of the oil indicative of the oil's quality, aging or contamination, the component capturing particles being secured to the sensor by a securing material and in which said sensor has at least one of the following features a) the component capturing inorganic particles comprise particles of titanium dioxide;
b) the securing material comprises a layer of an inorganic material;
c) the securing material comprises a layer of titanium dioxide;
d) the component capturing surface layer is produced by applying a mixture comprising the component capturing inorganic particles and precursors of the securing material to a surface of the sensor;
e) the securing material is substantially impermeable to the oil;
f) the component capturing surface layer comprises two or more types of component capturing inorganic particles, each type of component capturing inorganic particle being adapted to retain a different component or different combination of components of the oil indicative of its quality, aging or contamination.

14. The method of claim 13 comprising:
providing a pair of resonator sensors each having two major surfaces,
a single one of the pair of resonator sensors having at least one of the major surface of the sensor comprising
a component capturing surface layer provided with impression sites adapted to retain components of the oil indicative of the oil's quality, aging or contamination; immersing both major surfaces of both sensors in the oil to be monitored; and comparing the frequency shift between the two sensors.

15. The method of claim 13, in which the impression sites of the said sensor are produced by molecular imprinting.

16. The method of claim 13, in which the impression sites of said sensor are adapted to retain a set of components of the oil,
the said set of components of the oil comprising a plurality of different oil components which together provide an indication which is indicative of the oil's quality, aging or contamination.

17. The method of claim 13, in which the impression sites of said sensor are produced by molecular imprinting from at least one and preferably a plurality of components selected from the group consisting of capric acid, used oil components, and used oil.

18. The method of claim 13, in which the impression sites of said sensor are produced by molecular imprinting from at least one and preferably a plurality of components selected from the group consisting of fatty acids, fatty alcohols, fatty aldehydes and ketones, fatty peroxides and fatty esters.

19. The method of claim 13, in which the component capturing inorganic particles comprise particles of titanium dioxide and
the securing material comprises a layer of inorganic material.

* * * * *